United States Patent [19]

Skopek et al.

[11] 4,302,535

[45] Nov. 24, 1981

[54] ASSAY FOR MUTAGENESIS IN HETEROZYGOUS DIPLOID HUMAN LYMPHOBLASTS

[75] Inventors: Thomas R. Skopek, Somerville; Howard L. Liber, Brookline; Bruce W. Penman; William G. Thilly, both of Cambridge; Henry Hoppe, IV, Arlington, all of Mass.

[73] Assignee: Massachusetts Institute of Technology, Cambridge, Mass.

[21] Appl. No.: 79,549

[22] Filed: Sep. 27, 1979

[51] Int. Cl.³ .................... C12Q 1/68; C12Q 1/29; C12N 5/02
[52] U.S. Cl. ........................ 435/6; 435/29; 435/241
[58] Field of Search ............ 23/230 B; 424/2; 435/4, 435/6, 15, 172, 240, 241, 32, 29, 34, 39

[56] References Cited

U.S. PATENT DOCUMENTS 4,066,510 1/1978 Thilly ............................ 435/6

OTHER PUBLICATIONS

Clive, "A Linear Relationship Between Tumorigenic Potency in Vivo and Mutagenic Potency at the Heterozygous Thymidine Kinase (TK+/−) locus of L5178 Mouse Lymphoma Cells Coupled with Mammalian Metabolism", Chem. Abstracts, vol. 89, No. 3 (1978), p. 163, Abs. No. 18129w.

Trosko et al., "Sensitive Method to Measure Physical and Chemical Carcinogen induced unscheduled DNA Synthesis in rapidly dividing eukaryotic cells", Chem. Abstracts, vol 81, No. 25, (1974), Abs. No. 165808c.

Marquart et al., "Induction of Malignant Transformation and Mutagenesis in Cell Cultures by Cancer Chemotherapeutic Agents", vol. 40, No. 4, (1977), pp. 1930–1934.

Primary Examiner—Thomas G. Wiseman
Attorney, Agent, or Firm—Arthur A. Smith, Jr.; David E. Brook

[57] ABSTRACT

An assay is disclosed for determining mutagenic damage caused by the administration of a known or suspected mutagen to diploid human lymphoblastoid cell lines. The gene locus employed for this assay is the gene for thymidine kinase, uridine kinase, or cytidine deaminase. Since human lymphoblastoid cells contain two genes for these enzymes, heterozygotes of human lymphoblastoid cells are used in this assay.

7 Claims, 7 Drawing Figures

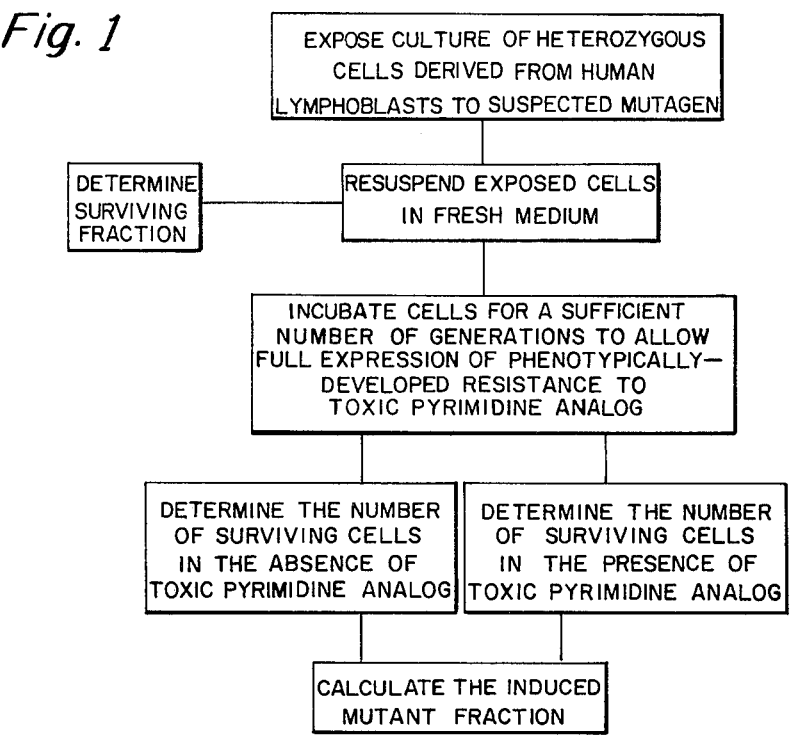
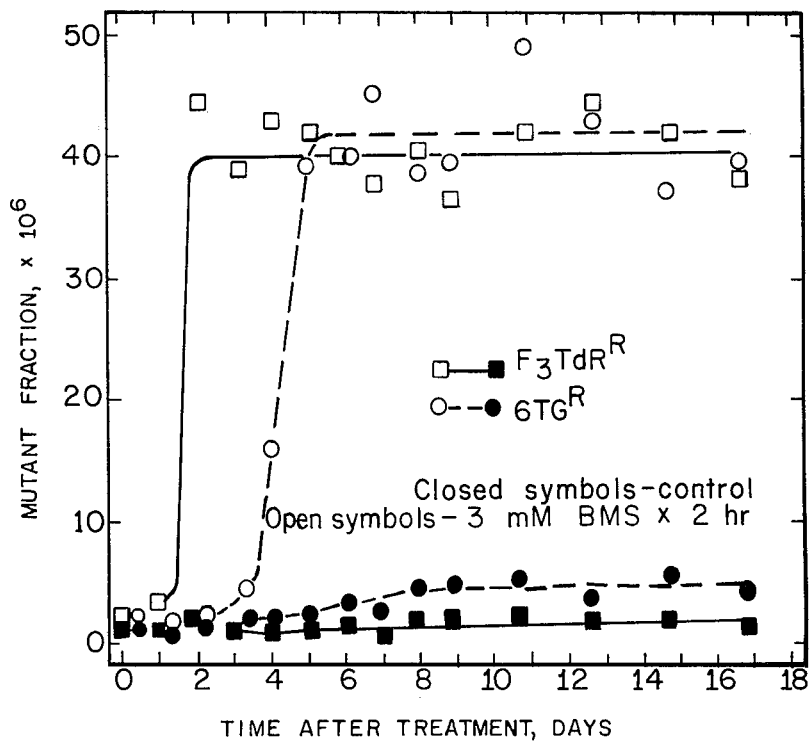

4,302,535

ASSAY FOR MUTAGENESIS IN HETEROZYGOUS DIPLOID HUMAN LYMPHOBLASTS

GOVERNMENT SUPPORT

Work relating to this invention was partially supported by grants from the National Institute of Health and U.S. Department of Energy.

TECHNICAL FIELD

This invention is in the field of biochemistry and specifically relates to genetic toxicology.

BACKGROUND ART

Two basic types of mutation assays have heretofore been employed which are reverse mutation assays and forward mutation assays.

A reverse mutation assay utilizes a mutant population that is deficient in some function, usually one involved in the synthesis of an essential cellular component. This deficiency results from an altered sequence of base pairs in the genetic material, DNA. This mutation renders the organism unable to grow unless supplemented with the missing component. The mutagenicity of a compound is defined by its ability to mutate the original DNA lesion back to the wild-type sequence or to suppress it by a second site mutation. The occurrence of such events can be detected by placing the treated population under selective (unsupplemented) conditions; only the revertants will grow and be detected. However, studies of the various molecular mechanisms of mutations have revealed that use of single reversion assays are not an acceptable method for screening chemical mutagens because particular mutagens cannot cause all types of mutations. Thus, sets of reversion assays are employed to reduce the probability of missing the activity of a mutagen.

In a forward mutation assay, a population of cells is treated with a suspected mutagen and then exposed to a selective agent which is toxic to wild-type cells. Mutants which lack the cellular function necessary for the toxic effect of the selective agent, such as an enzyme, can survive and be detected.

Assays for mutagenesis, both reverse and forward, have often been based upon bacterial cells or mammalian cells such as rodent cells. For example, McCann et al. have developed an assay employing *S. typhimurium* histidine reversion whereas Clive et al. have developed a forward mutation assay in L$_{5178}$Y mouse lymphoma cells using the thymidine analog bromodeoxyuridine as the selective agent. See McCann, J., Choi, E., Yamasaki, E. and Ames, B. N. (1975) *Proc. Natl. Acad. Sci.*, 72: 5135; Clive, D. and Spector, J. F. S. (1975) *Mutat. Res*, 31, 17–29; Clive, D., Flamm, W. G. Machesko, M. R., and Bernheim, N. J. (1972) *Mutat. Res*, 16, 77–87; and Clive, D., Flamm, W. G., and Patterson, J. B. (1973) *Chemical Mutagens: Principles and Methods for their Detections*, Vol. 3, pp. 79–103, Plenum Publishing Co., New York. There are, however, important species differences in DNA/chromatin structure, DNA repair, membrane structure, and metabolism between human cells and bacterial and/or other mammalian cells.

One recently developed assay for mutagenesis is a forward mutation assay involving human diploid lymphoblast cells. This assay detects mutagenic damage at the hypoxanthine guanine phosphoribosyl transferase gene locus based upon the resistance of mutant lymphoblasts to purine analogs, such as 6-thioguanine, which serves as a substrate for this enzyme and is toxic to non-mutant lymphoblasts. While this assay appears to be quite promising, it does involve a relatively long phenotypic expression time (10–12 generations) before the resistance to the purine analog is completed. A complete description of this assay is presented in U.S. Pat. No. 4,066,510 issued to William G. Thilly.

DISCLOSURE OF THE INVENTION

This invention relates to an assay for determining mutagenesis by employing human diploid or near-diploid cells capable of continuous division in suspension culture. The cells employed are selected for the characteristic of having only one functional copy of the gene for any of a number of enzymes necessary for the conversion of pyrimidines or their analogs into nucleic acids, RNA or DNA. Examples of such enzymes include thymidine kinase, uridine kinase, and cytidine deaminase.

The assay is performed by exposing a culture of such cells to an agent to be tested for mutagenicity. Exposed cells are then incubated for the number of generations which allow full expression of their phenotypically-developed resistance to a pyrimidine analog which acts as a substrate for the enzyme involved and, when acted upon by the enzyme, becomes toxic to normal cells. After this resistance has been fully expressed, the number of cells which can grow is then determined in the presence of the selective agent and without selective agent to determine the potency of the test agent as a mutagen.

Metabolizing systems can also be added to the cultures to determine whether any metabolite by-products of a tested compound are mutagens.

This assay permits the continuous growth of treated suspension cultures which obviates the physical manipulation (passaging) needed to maintain growth of an anchorage-dependent cell lines. It also has a major advantage because it can be performed using cell lines derived from human diploid lymphoblasts, rather than lower mammalian cells or bacterial cells. In addition, the period for full phenotypic expression of the resistance to the pyrimidine analog has been found to be significantly shorter than prior forward mutation assays involving human diploid lymphoblast cell lines.

BRIEF DESCRIPTION OF THE DRAWINGS

FIG. 1 is a flow diagram illustrating the mutagenesis assay protocol described herein;

FIG. 2 is a graphical presentation of the phenotypic expression time of trifluorothymidine-resistance and 6-thioguanine resistance in cell line TK6 induced by butylmethane sulfonate;

BEST MODE OF CARRYING OUT THE INVENTION

Figure 3:
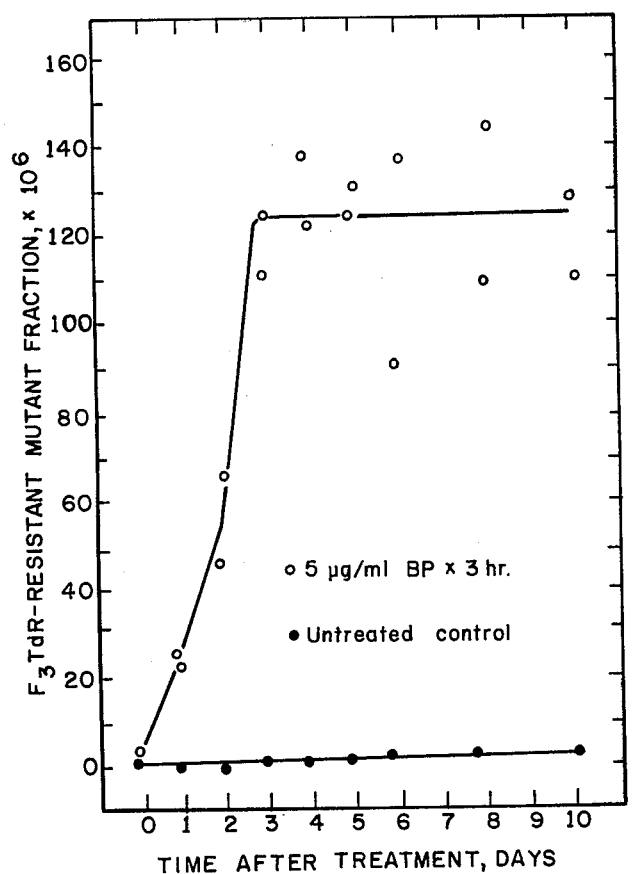
FIG. 3 is a graphical presentation of the phenotypic expression time of trifluorothymidine-resistance in cell line TK6 induced by Benzo(alpha)pyrene in the presence of a metabolizing system derived from rat liver.

The invention will now be further described, sometimes with particular reference to the Figures.

Referring now to FIG. 1, it can be seen that the first step in the mutagenesis assay is the exposure of a culture of heterozygous cells derived from human lymphoblasts to a suspected mutagenic agent.

The necessity for employing heterozygous cells can be understood with reference to thymidine kinase.

Thymidine kinase is an enzyme which, in the presence of adenosine triphosphate and $Mg^{++}$ phosphorylates deoxythymidine to form thymidylic acid. Thymidine kinase also phosphorylates a number of thymidine analogs, including bromodeoxyuridine, iododeoxyuridine, and trifluorothymidine. These analogs, once phosphorylated, are toxic to cells, either because of inhibitory properties or because of incorporation into nucleic acids. There are, however, two copies of the thymidine kinase gene in each cell. In practical terms, a large number of cells would have to be observed in order to find a cell with two inactive thymidine kinase genes. Because of this, thymidine kinase heteroxygotes are derived which have only one intact thymidine kinase gene for use in this assay.

Such heterozygotes can be derived from lymphoblasts by exposing lymphoblasts to a potent frameshift mutagen, such as ICR-191, to enrich for mutants. This produces $TK^{-/-}$ homozygotes, and one of these can be selected and treated again with the mutagen to produce the desired $TK^{+/-}$ heteroxygote since ICR-191 has the property of reverting the mutations it causes.

In the case of chemical mutagens, these can simply be added to the culture suspension of heteroxygous cells. Physical agents, such as electromagnetic or nuclear radiation, can also be used. For example, a culture of growing heterozygous cells can be irradiated with ultraviolet light to test for mutagenesis. Other conditions, such as heat, cold, or exposure to other microorganisms, such as viruses, can also be used to cause mutagenesis.

It is desirable to establish exponential cell growth prior to mutagen exposure. The dosage of mutagen, exposure time, etc., can vary widely. It is believed that any dosage and/or exposure can be used as long as some sufficient fraction of the treated cells survive. To determine this, the exposed cells are resuspended after exposure to the mutagen in fresh medium and the surviving fraction is determined by plating. In cases where the mutagen being tested is exceptionally cytotoxic, it is necessary to use more cells initially. In a typical assay, the cells are exposed to a suspected chemical mutagen for about 24 hours, but there is nothing critical about this time and wide variations are possible.

After treatment, there is a period before cell growth and division provides a sufficient number of live cells to allow the determination of mutant fraction. This is known as the "grow back" period. In the work described herein, it has been noted that this period varies significantly for different mutagens studied. It may also vary with dosage, particular cell line employed, culture conditions, etc.

The degree of mutagenesis caused by exposure to the mutagen is related to the expression of resistance to a pyrimidine analog, such as trifluorothymidine, which is normally toxic to non-mutant cells. Cells capable of forming clones in the presence of trifluorothymidine have lost, via mutation, the ability to synthesize active thymidine kinase, which means that the toxic pyrimidine analog is not incorporated into the nucleic acid, DNA or RNA.

It has been found that a typical period for full phenotypic expression of trifluorothymidine resistance is about two days.

After the period of time for full phenotypic expression of cell resistance has passed, the induced mutant fraction can be determined. This is determined by first determining the fraction of exposed cell population that is mutant; comparing that fraction of mutant cells to a control; and then calculating the induced mutant fraction from these. Thus, the mutant fraction is equal to the ratio of cell cloning efficiency in the presence of the pyrimidine analog substrate to the cloning efficiency in its absence. It has been found that the induced mutant fraction is stable after sufficient time has been allowed for full phenotypic expression of the cell resistance for human diploid lymphoblastoid cells treated with known mutagenic agents. This is, of course, characteristic of true mutagenic cell damage.

The selective agents employed as markers are pyrimidines or pyrimidine analogs which are toxic to non-mutant cells. Examples include: substituted pyrimidines, such as fluorouracil; thymidine ribosides, such as trifluorothymidine; pyrimidine deoxyribosides, such as chloro-, bromo-, iododeoxyuridine.

The cell lines used in most of the actual experimental work described herein are lines of human lymphoblasts which are clonal derivatives of WIL-2 diploid human lymphoblasts, originally isolated from a male spherocytosis patient. One of these sub-clones is known as TK6, which has been deposited at the American Type Culture Collection and has received the number ATCC-CRL 8015. Other similar sub-clones, which are heterozygous at the thymidine kinase locus, are available from the genetic toxicology group at the Massachusetts Institute of Technology.

Other diploid or near-diploid human lymphoblast type cell lines or diploid human cell lines capable of continuous division in suspension culture are also suitable for use in this assay. It is, of course, necessary that such lines contain one and only one gene copy for the cellular function responsible for converting the pyrimidine analog into a toxic metabolite.

Standard incubation and culturing techniques, as well as standard culture media, with or without supplements, can be used with such cell lines. Those skilled in the art will be able to ascertain, with no more than routine experimentation, other suitable cell lines and the preferred growth conditions for any particular line.

Although most of the experimental work described herein was performed using trifluorothymidine, other pyrimidine analogs which are toxic for the heterozygote cells are also suitable. As mentioned above, other suitable thymidine analogs include bromodeoxyuridine and iododeoxyuridine. Additionally, if other gene loci are used, then additional pyrimidine analogs can be employed. For example, if the uridine kinase gene locus is employed, a suitable pyrimidine analog toxic to non-mutant cells is 5-fluorouridine. Similarly, if the gene locus employed is the cytidine deaminase locus, a suitable pyrimidine analog is 5-fluorodeoxycytidine.

It is often necessary to add a drug-metabolizing system to the mutagenesis assay described herein. This is because the enzyme systems represented by the cell microsomes often catalyze chemical reactions producing genetically active derivatives from inactive precursors. In assays such as that described herein, the lymphoblast cells grow rapidly in culture and do not express significant drug-metabolizing activity. The addition of any of a number of active drug-metabolizing systems to these cell cultures, therefore, makes a more complete bioassay system. Any of the well known metabolizing systems, including those obtained from post-mitochrondrial supernatant (PMS) obtained from the liver of various mammals and suitably treated are suitable herein.

The following examples further illustrate the invention.

EXAMPLE 1

ISOLATION OF A HUMAN LYMPHOBLASTOID LINE HETEROZYGOUS AT THE THYMIDINE KINASE LOCUS

The original lymphoblastoid line employed was HH4, which was derived from the near diploid WIL-2 line, originally isolated from a male spherocytosis patient. Unlike most other diploid lymphoblast lines, HH4 can form macroscopic colonies in soft agar in absence of a feeder layer of human fibroblasts.

Initially, approximately $2 \times 10^8$ TK+/+ HH4 cells (about $5 \times 10^5$/ml) were twice treated with ICR-191 in stationary culture in RPMI 1640 medium, supplemented with 15% fetal calf serum. Four days after the last treatment, 1 microgram/ml trifluorothymidine was added to the culture which was then left at 37° C. for three days to further enrich for mutants. The culture was then plated in the presence of one $\mu$g/ml trifluorothymidine in RPMI medium supplemented with 20% FCS and solidified with 0.25% Agarose.

Ten trifluorothymidine-resistant clones were isolated and purified. To determine if the mutants isolated were actually TK−/−, a TK enzyme assay was performed. The TK enzyme assay employed was a modification of the method developed by Furlong. See Furlong, N. B. (1963), Anal. Biochem., 5, 515–522.

Approximately $10^8$ cells were washed in saline and resuspended in 1 ml of 0.1 M Tris-HCl with 2.5 mM mercaptoethanol. The cell suspension was sonicated with four 15-second bursts and then centrifuged at 9000 g for 30 minutes at 0° C. The supernatant (cell sap) was then decanted. Each reaction mixture contained the following: 40 $\mu$l cell sap, 40 $\mu$l 0.1 M Tris-HCl buffer (pH 8.0), and 20 $\mu$l H$_2$O containing 50 $\mu$MTdR and 0.005 $\mu$moles [$^3$H]-TdR (200 mCi/m mole), 0.5 $\mu$moles ATP, 0.6 $\mu$moles $\alpha$-glycerophosphate, and 0.5 $\mu$moles MgCl$_2$. The reaction was run in plastic conical 15 ml centrifuge tubes (Falcon Plastics, Oxnard, Calif.). The tubes were incubated at 37° C. for 30 minutes, and then immersed in boiling water for 2 minutes to terminate the reaction. The tubes were then centrifuged at 2000 rpm for 15 minutes to precipitate the denatured protein. The supernatants were decanted and 20 $\mu$l samples were taken and spotted on Whatman DE81 filter papers. The filters were washed in a chimney apparatus with 20 ml 5 mM NH$_4$HCO$_3$ followed by 20 ml ethanol. The filters were then dried and added to 10 ml Aquasol and counted.

Each mutant possessed approximately 5% of the activity of the parent TK+/+ population. This residual activity was probably due to mitochondrial TK released by sonication. Mitochondrial TK is so compartmentalized as to not participate in the synthesis of toxic pyrimidine analogs.

To isolate the TK+/− heterozygote, one of the TK−/− clones was selected and approximately $10^8$ cells were twice treated with ICR-191. These treatments were 24-h treatments with 0.5 $\mu$g/ml of ICR-191. Three days after the final treatment, the culture was plated in CHAT medium supplemented with 20% FCS and solidified with 0.25% Agarose. CHAT medium consisted of RPMI supplemented with $1 \times 10^{-5}$ M cytidine, $2 \times 10^{-4}$ M hydoxanthine, $2 \times 10^{-7}$ M aminopterin, and $1.75 \times 10^{-5}$ M thymidine.

Nine CHAT resistant clones were isolated. The mutants were tested for TK enzyme activity and found to have only 25–50% of the wild-type (TK+/+) level. Thus, these nine clones represent TK heterozygotes (TK+/−) suitable for the assay of mutations to the absence of TK (TK−/−) described herein.

EXAMPLE 2

MUTATION ASSAY EMPLOYING TK6 CELL LINE

One cell line, TK6, isolated in Example 1, was maintained in spinner culture at 37° C. with a doubling time of approximately 18 hours. Approximately $10^7$ cells ($4 \times 10^5$/ml) were treated with either BMS (1 mM) of ICR-191 (0.25 $\mu$g/ml and 0.50 $\mu$g/ml) for 24 hours. After treatment, the cells were centrifuged and resuspended in fresh medium at a concentration of $3 \times 10^5$/ml. Dilutions to $3 \times 10^5$/ml were made daily.

At various times after treatment, duplicate aliquots of $4 \times 10^6$ cells were centrifuged and resuspended in 10 ml of RPMI containing 20% FCS, 100 $\mu$/ml penicillin, and 0.25% agarose (plating agar). To determine the plating efficiency of the culture, a 10 $\mu$l sample of the suspension containing 4000 cells was added to 5 ml of plating agar and layered over 5 ml prejelled layer of the same medium in a 100 mm petri dish. A 10 $\mu$l aliquot of 2 mg/ml solution of trifluorothymidine (TFTdR) was added to the 10 ml suspension. The suspension was then plated in two 5 ml aliquots, each layered over a prejelled layer of plating agar in a 100 mm petri dish (final TFTdR concentration = 1 $\mu$g/ml). The plates were fed the following day with 3 ml of medium.

The plates were counted after 7–10 days in a 37° C., 5% CO$_2$, humidified incubator.

Results from the mutation assay with BMS and ICR-191 are presented in Table 1.

TABLE 1

Induction of TFTdR-resistant Mutants in H$_2$BT Following Treatment with ICR-191 and BMS

| Compound and Dose | Days Post-Treatment | Observed Mutants per $4 \times 10^6$ Cells | Plating Efficiency | Calculated Mutant Fraction $\times 10^6$ |
|---|---|---|---|---|
| ICR-191 | 0 | 26 | 0.25 | 26 |
| (0.25 $\mu$g/ml × 24 Hrs) | 2 | 139 | 0.26 | 130 |
|  | 4 | 126 | 0.27 | 120 |
| ICR-191 | 0 | 55 | 0.24 | 57 |
| (0.5 $\mu$g/ml × 24 Hrs) | 2 | 229 | 0.25 | 230 |
|  | 4 | 182 | 0.20 | 230 |
| BMS | 1 | 132 | 0.094 | 350 |
| (1 mM × 24 Hrs) | 3 | 275 | 0.15 | 460 |
|  | 5 | 387 | 0.23 | 410 |
| 0 CONTROL | 1 | 1 | 0.23 | 1.1 |
|  | 3 | 1 | 0.22 | 1.1 |

TABLE 1-continued

Induction of TFTdR-resistant Mutants in H₂BT Following Treatment with ICR-191 and BMS

| Compound and Dose | Days Post-Treatment | Observed Mutants per 4 × 10⁶ Cells | Plating Efficiency | Calculated Mutant Fraction × 10⁶ |
|---|---|---|---|---|
| | 5 | 3 | 0.35 | 2.1 |

EXAMPLE 3

ADDITIONAL MUTATION ASSAYS WITH TK6

Additional mutation experiments were performed with the TK6 cell line using resistance to 1 μg/ml trifluorothymidine as the selective agent. Mutagens examined included butylmetanesulfonate, ICR-191, and benzo(alpha)pyrene. The treatment of the cells was done in RPMI 1640 medium supplemented with 15% fetal calf serum. The concentrations and time of treatment are given below together with the induced mutant fraction found. Incubation was in stationary culture in a humidified, 5% $CO_2$ incubator at 37° C. After treatment, cells were centrifuged, resuspended in fresh medium, and grown for at least three days before plating in 1.0 μg/ml trifluorothymidine. The results were:

| Treatment | $F_3TdR^R$ MF × 10⁶ |
|---|---|
| NONE*+ | 1–4 |
| BMS, 1.0 mM × 24 hr+ | 400 |
| BMS, 3.0 mM × 2 hr* | 40 |
| ICR-191, 0.25 μg/ml × 24 hr+ | 120 |
| ICR-191, 0.5 μg/ml × 24 hr+ | 210 |
| B(α)P, 5 μg/ml × 3 hr in 5% (v/v) PMS* | 120 |

*Plating in microtiter culture
+Plating in soft agarose

EXAMPLE 4

GROWTH OF TRIFLUOROTHYMIDINE-RESISTANT MUTANTS IN VARIOUS MEDIA

A series of clones resistant to trifluorothymidine, which were induced by butylmethanesulfonate or ICR-191, were examined for their ability to grow in trifluorothymidine and in CHAT medium.

These mutants were isolated from soft agarose plates in which at least a 100-fold increase in mutant fraction had been observed, and then purified by recloning under selective conditions. Growth experiments were performed approximately three weeks later, in 25 cm² T-flasks with 15 ml total volume. $T_2$'s are doubling times calculated from growth curves. RPMI is normal medium with 15% fetal calf serum. $F_3TdR$ was 1.0 μg/ml. CHAT contained $1 \times 10^{-5}$ M cytidine, $2 \times 10^{-4}$ M hypoxanthine, $2 \times 10^{-7}$ M aminopterin, and $1.75 \times 10^{-5}$ M thymidine. NG means no growth was observed in 3 days. The results are presented in Table 2 as follows:

TABLE 2

| Mutant | $T_2$ - RPMI | $T_2$ - $F_3TdR$ | $T_2$ - CHAT |
|---|---|---|---|
| BMS-2 | 18.6 | 18.4 | NG |
| BMS-3 | 18.1 | 19.2 | NG |
| BMS-4 | 17.3 | 17.7 | NG |
| BMS-5 | 20.1 | 19.7 | NG |
| ICR-1 | 18.2 | 18.6 | NG |
| ICR-2 | 21.0 | 21.2 | NG |

TABLE 2-continued

| Mutant | $T_2$ - RPMI | $T_2$ - $F_3TdR$ | $T_2$ - CHAT |
|---|---|---|---|
| TK6 | 17.5 | NG | 17.5 |

As the data in Table 3 indicate, all mutants grew well in $F_3TdR$. But not at all in CHAT. This is the expected phenotype for TK$^{-/-}$ cells.

EXAMPLE 5

PHENOTYPIC EXPRESSION TIME

TK6 cells were treated with the direct acting mutagen butylmethane sulfonate or the PMS-dependent mutagen benzo(alpha)pyrene in order to determine the phenotypic expression time. The TK6 cells were treated in duplicate with 3 mM BMS for 2 hours and plated from T=0 to T=17 days for resistance to 1 μg/ml trifluorothymidine and 5 μg/ml 6-thioguanine. The resulting data are plotted in FIG. 2 for BMS, wherein each point is the average of 2 values computed for each day.

TK6 cells were treated in duplicate with 5 μg/ml BP for 3 hours in the presence of 5% (v/v) rat liver postmitochondrial supernatant. They were then plated on days 0–10 in 1 μg/ml of trifluorothymidine, and the data produced are plotted in FIG. 3. As can be seen from FIGS. 2 and 3, the expression time was two days for the trifluorothymidine-resistance locus, as compared to 5–6 days for the 6-thioguanine resistance.

EXAMPLE 6

OPTIMIZATION OF SELECTIVE AGENT CONCENTRATION

Figure 4:
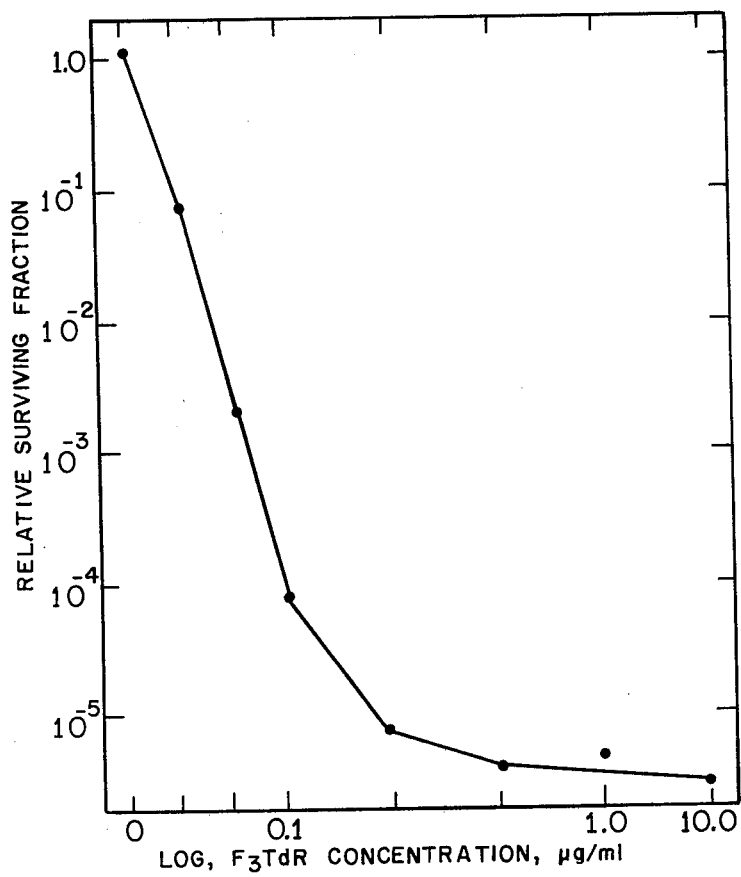
FIG. 4 is a graphical presentation of the toxicity of trifluorothymidine at various concentrations to cell line TK6.

Optimization of the selective agent concentration was examined by plating TK6 cells in different concentrations of trifluorothymidine. The TK6 cells were plated on microtiter plates in different concentrations of trifluorothymidine and scored for surviving fractions two weeks later. FIG. 4 is a plot of the data obtained wherein each point is the average of two independent platings. FIG. 4 demonstrates that from 0.33 μg/ml through 10 μg/ml, there is no difference in the observed mutant fraction of an untreated culture.

Table 3 shows that the plating efficiency of induced mutants is unaffected by 1 μg/ml trifluorothymidine within the limits of experimental error.

TABLE 3

| Mutant | PE in RPMI | PE in RPMI - $F_3TdR$ | PE in RPMI-$F_3TdR$ with 40,000 TK6/well |
|---|---|---|---|
| BMS-2 | 0.11 | 0.09 | 0.09 |
| BMS-3 | 0.19 | 0.21 | 0.17 |
| BMS-4 | 0.16 | 0.11 | 0.15 |
| BMS-5 | 0.29 | 0.29 | 0.31 |
| ICR-1 | 0.17 | 0.21 | 0.21 |
| ICR-2 | 0.13 | 0.09 | 0.10 |

The effect of dead TK6 cells on the expression of mutants growing in microtiter plates was also studied. The data in Table 3 show that the mutants apparently plate without loss of efficiency either in or out of the presence of TK6.

EXAMPLE 7

RECONSTRUCTION EXPERIMENT

Figure 5:
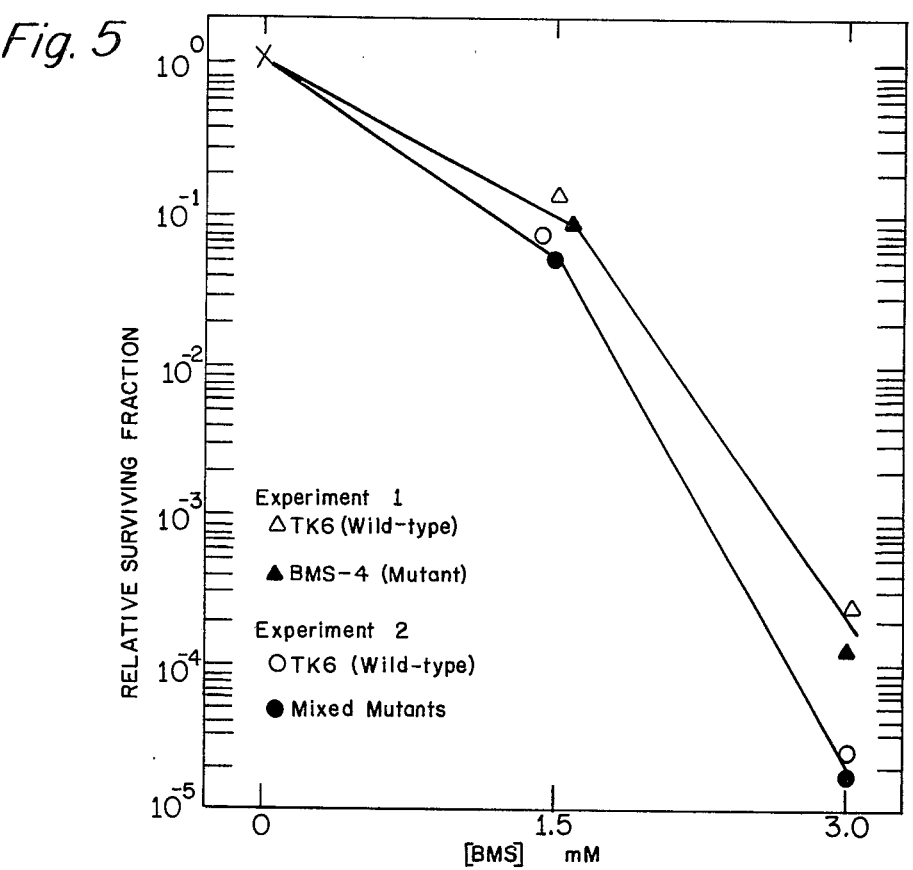
FIG. 5 is a graphical presentation of the toxicity of butylmethane sulfonate to wild-type and trifluorothymidine-resistant TK6 lymphoblasts.

In order to show that mutants were not preferentially selected by differential toxicities of mutagens, it was demonstrated that BMS was equally toxic to TK6 and a mixture of mutants or a single mutant clone. TK6 cells were exposed to BMS for 24 hours. After treatment, the relative surviving fraction was determined by plating in micro wells. Mixed mutants were a mixture of 6 different trifluorothymidine resistant clones. Data from two experiments performed on different days are presented in FIG. 5. As can be seen, the data indicate that mutants die with the same kinetics as wild-type (TK6) cells, thus eliminating the possibility of selective differentiation between mutants and non-mutants.

EXAMPLE 8

ASSAY FOR MUTAGENICITY OF POLYAROMATIC HYDROCARBONS

Three polyaromatic hydrocarbons derived from kerosine soot were examined for mutagenicity. These were benzo(alpha)pyrene, fluoroanthene, and perylene.

Figure 6:
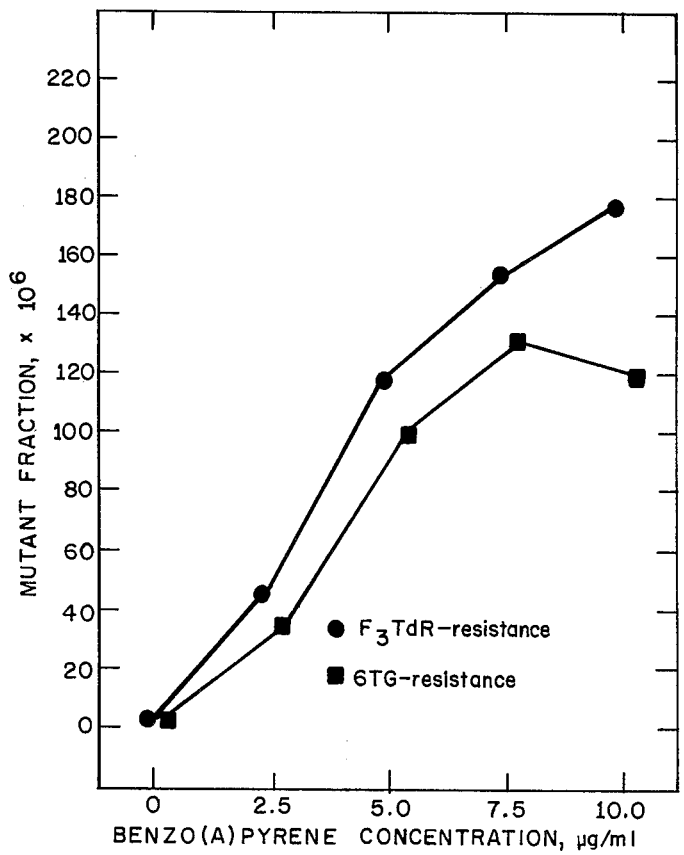
FIG. 6 is a graphical presentation of the mutagenicity of benzo(alpha)pyrene to TK6 cells measured by the appearance of trifluorothymidine or thioguanine resistant mutants.

TK6 cells were treated with benzo(alpha)pyrene in duplicate for 3 hours in the presence of 5% (v/v) rat liver post-mitochondrial supernatant and plated for trifluorothymidine resistance (1 μg/ml) and 6-thioguanin(5 μg/ml). Data obtained for benzo(alpha)pyrene) are presented in FIG. 6, wherein the points shown are the average mutant fractions. Error bars are the standard deviation of the mean.

Figure 7:
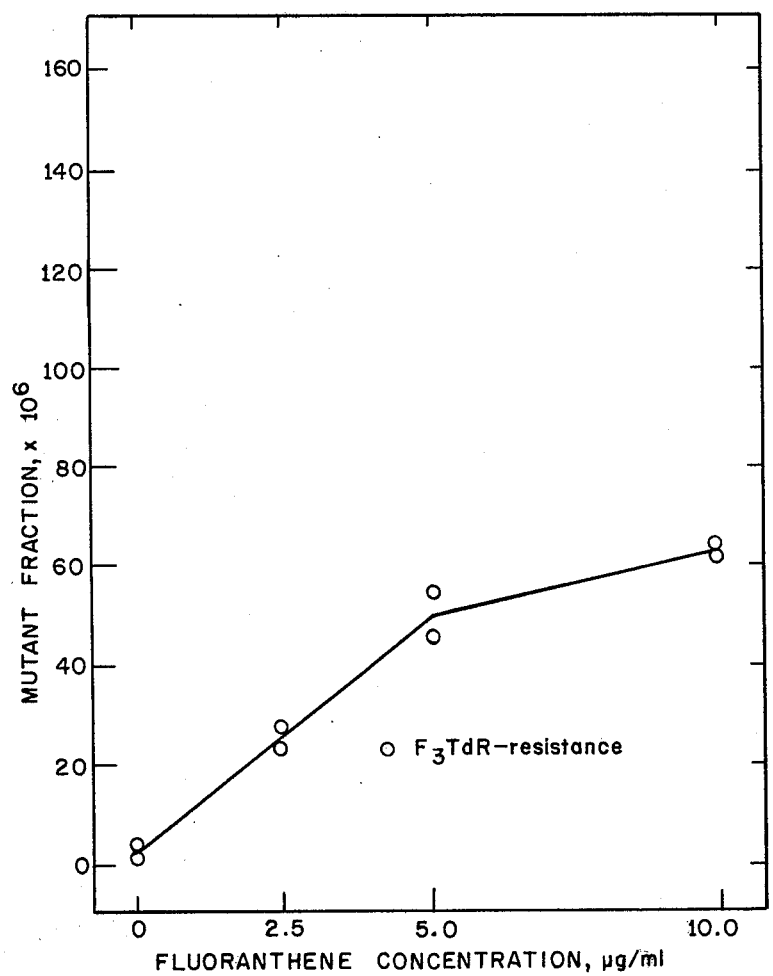
FIG. 7 is a graphical presentation of the mutagenicity of fluoranthene to TK6 cells.

A similar assay employing TK6 cells was done for fluoranthene and the cells were plated on days 3 and 6 for trifluorothymidine resistance. Data obtained for fluoranthane are shown in FIG. 7.

For perylene, TK6 cells were treated in duplicate with perylene for 3 hours in the presence of 5% (v/v) aroclor-induced rat liver post-mitochondrial supernatant. They were plated in microtiter dishes for trifluorothymidine resistance (1 μg/ml) on days 3 and 5, and for 5-thioguanine resistance (5 μg/ml) on days 5 and 7 following treatment. Benzo(alpha)pyrene was a positive control, at 5 μg/ml for 3 hours. The resulting data are presented in Table 4 presented below.

TABLE 4

| Concentration (μg/ml) | $F_3TdR^R$ MF × $10^6$ | Avg | $6TG^R$ MF × $10^6$ | Avg |
|---|---|---|---|---|
| 0A | 3.0, 2.2 | | 6.8, 2.8 | |
| 0B | 3.2, 4.3 | 3.2 | 5.5, 3.9 | 4.7 |
| 2.5A | 2.9, 2.6 | | 4.5, 3.0 | |
| 2.5B | 3.7, 4.1 | 3.3 | 2.8, 4.7 | 3.8 |
| 5.0A | 4.5, 3.8 | | 5.8, 6.0 | |
| 5.0B | 3.4, 3.1 | 3.7 | 6.7, 2.8 | 5.4 |
| BP A | 136, 128 | | 119, 75 | |
| BP B | 150, 95 | 129 | 84, 96 | 94 |

TABLE 4-continued

As can be seen from the above plots and tables, benzo(alpha)pyrene and fluoroanthene were active as mutagens for these human cells, but perylene was inactive.

Industrial Applicability

This invention has industrial applicability in the testing of chemical compounds or other agents for their potential mutagenicity in human cells.

Equivalents

Those skilled in the art will recognize or be able to ascertain using no more than routine experimentation many of equivalents to the specific embodiments of the invention described herein. Such equivalents are intended to be covered by the following claims.

We claim:
1. An assay for determining mutagenesis, comprising:
   a. exposing a culture of human diploid or near-diploid cells capable of continuous division in suspension culture, said cells being heterozygotes having only one active gene for an enzyme for converting a pyrimidine analog to a toxic material for said cells to an agent to be tested for its mutagenic effects on said cells;
   b. incubating exposed cells for a number of generations to allow full expression of phenotypically-developed resistance to a pyrimidine analog which acts as a substrate for said enzyme and is normally toxic to said cells;
   c. culturing cells having the full phenotypically developed resistance both in the presence of and without a pyrimidine analog which is toxic to non-mutant cells; and,
   d. comparing the amount of mutant cells to the amount of non-mutant cells to thereby determine the degree of induced mutagenesis.
2. An assay of claim 1 wherein the active gene codes for thymidine kinase, uridine kinase or cytidine deaminase.
3. An assay of claim 2 wherein said cells comprise a heterozygote of human diploid lymphoblasts.
4. A method of claim 3 wherein said pyrimidine analog comprises a 5-halodeoxyuridine or 5-halothymidine.
5. An assay of claim 4 wherein an active drug-metabolizing system is also added to the cell culture.
6. An assay of claims 1 or 5 wherein the pyrimidine analog comprises trifluorothymidine.
7. An assay of claim 6 wherein the active gene codes for thymidine kinase.

* * * * *